United States Patent [19]

Vartsky et al.

[11] Patent Number: 4,941,162
[45] Date of Patent: Jul. 10, 1990

[54] METHOD AND SYSTEM FOR DETECTION OF NITROGENOUS EXPLOSIVES BY USING NUCLEAR RESONANCE ABSORPTION

[75] Inventors: David Vartsky, Rehovot; Mark Goldberg, Rehovot; Amos Breskin, Rehovot; Gideon Engler, Rehovot; Aharon Goldschmidt, Nes Ziona; Ephraim Izak, Rishon Le-Zion; Ovadia Even, Givataim, all of Israel

[73] Assignee: The State of Israel, Atomic Energy Commission, Soreq Nuclear Research Center, Yavne, Israel

[21] Appl. No.: 369,230

[22] Filed: Jun. 22, 1989

[30] Foreign Application Priority Data
Jun. 22, 1988 [IL] Israel .................................. 86826

[51] Int. Cl.$^5$ .................................. G01N 23/04
[52] U.S. Cl. .................................. 378/3; 378/53; 378/57
[58] Field of Search .................................. 378/3, 53, 57

[56] References Cited

U.S. PATENT DOCUMENTS 3,612,875  10/1971  Ord .................................. 378/3

Primary Examiner—Craig E. Church
Attorney, Agent, or Firm—Browdy and Neimark

[57] ABSTRACT

A method for the detection of a nitrogenous explosive material in an object is provided which makes use of nuclear resonance absorption. The object to be tested is placed between a 9.17 MeV γ-rays source and an γ-rays detector holding a nitrogen medium. The total and the non-resonant attenuation of the γ-rays flux is read by the detector and fed into a recorder. From the measured attenuation the net non-resonant attenuation is calculated and the amount of a nitrogenous explosive present in the object is determined therefrom.

Also provided by the invention is a system for detecting a nitrogenous explosive in an object.

8 Claims, 4 Drawing Sheets

CROSS-SECTION FOR ABSORPTION
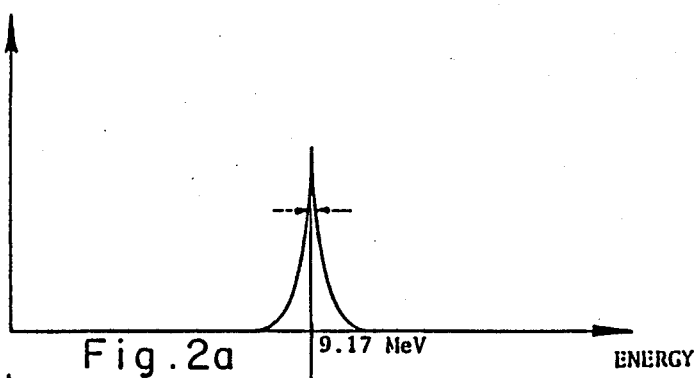
Fig.2a  9.17 MeV  ENERGY
INCIDENT FLUX
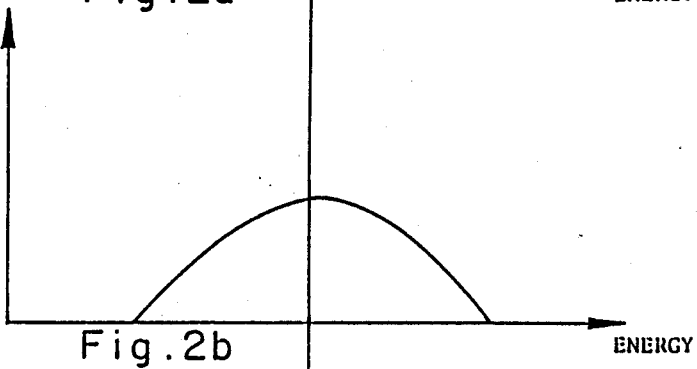
Fig.2b  ENERGY
TRANSMITTED FLUX
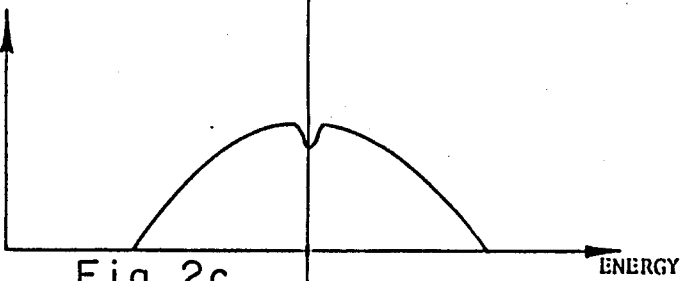
Fig.2c  ENERGY
DETECTION EFFICIENCY
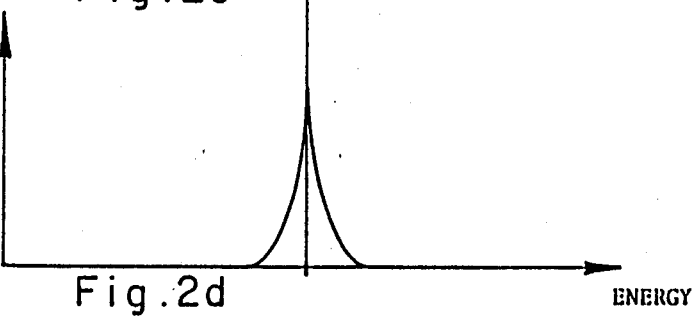
Fig.2d  ENERGY

METHOD AND SYSTEM FOR DETECTION OF NITROGENOUS EXPLOSIVES BY USING NUCLEAR RESONANCE ABSORPTION

FIELD OF THE INVENTION

The present invention concerns a method and system for detection of nitrogenous explosives by using nuclear resonance.

BACKGROUND OF THE INVENTION AND PRIOR ART

The detection of explosives has become a highly important issue in recent years, especially because of the increasing occurrence of terrorist activities all over the world. Searching for explosives by security personnel is nowadays a matter of course in many public places and installations such as airports, government edifices, army and police installations and the like. In many instances such searches are carried out by manual inspection of people's belongings and may occasionally also involve the employment of dogs trained to sniff explosives. It is also customary to X-ray personal belongings in order to detect suspicious objects; but generally, indications obtained in this way are considered inconclusive and as a rule, when something suspicious is detected a follow-up manual inspection is required.

Until now no reliable method for swift and sensitive detection of explosives has been developed.

Nuclear resonance fluorescence is a process in which a nucleus is raised to an excited state by absorbing an incident photon. The excited nucleus may decay by emission of either a photon - $(\gamma,\gamma)$ reaction known as nuclear resonance scattering (NRS) or by a particle emission, e.g. a $(\gamma,p)$ reaction. Such decay or de-excitation is characterized by the emission of $\gamma$-radiation of specific energies which correspond to certain discrete energy levels of the atomic nucleus and which are atom-specific. Consequently in NRS it is possible to detect a given substance in a mixture by irradiating the mixture with $\gamma$-rays having an energy that corresponds to the energy level to which the sought-after atom could be excitable. If that atom is present in the mixture there occurs a resonant absorption which in turn produces fluorescence detectable by photon detectors that are in common use.

The main use of NRS is in research, e.g. for determining half-lives of excited nuclear state of various atoms, but some analytical methods based on NRS were developed for application in medicine, e.g. for detection of excessive amounts of iron in the liver, and also in the mineral industry, e.g. for detection of copper and nickel in minerals. These methods are, however, inapplicable in detecting nitrogenous explosives since the partial electromagnetic widths for ground state transitions from most excited states of nitrogen is very low and, therefore, NRS thereof is barely detectable.

BRIEF DESCRIPTION OF THE INVENTION

In accordance with the invention it has been found that as distinct from NRS, nuclear resonance absorption (NRA) is suitable and effective for the detection of nitrogen concentrations in inspected objects. In this method the transmitted portion of the incident photon flux is measured, rather than the scattered flux as in NRS. This approach enables the recording of spatial information and may therefore be called resonant radiography.

The probability (cross-section) for excitation of a nucleus by photons as function of photon energy exhibits resonant behaviour, i.e. it is largest when the energy of the incident photon corresponds to the excitation energy of the nuclear level. Each nuclear level has a specific cross-section for absorbing the incident photon depending on level parameters such as energy, partial width of direct $\gamma$-transition to the ground state - $\Gamma\gamma_0$, total width of the level $\Gamma$, angular momentum and doppler width - $\Delta$. In general, a nuclear level can be applied to nuclear resonant radiography if the following conditions are met:

The ratio $\Gamma\gamma_0/\Gamma_T \geq 0.01$

The ratio $\Delta/\Gamma_T < 1$

Investigations conducted in accordance with the present invention revealed that in nitrogen ($^{14}$N) only the properties of the 9.17 MeV level are such that the absorption cross-section is adequate for resonant absorption radiography. In practice, the resonant component of attenuation in nitrogen, if present, is superimposed on the non-resonant attenuation, which is undergone by $\gamma$-rays in all materials. Experimentally, the two quantities directly determined are the total attenuation (resonant and nonresonant) and the non-resonant component. The net resonant attenuation, which is the quantity underlying the present invention, is extracted from these two quantities and is indicative of the amount of nitrogen traversed by the $\gamma$-rays. For the 9.17 MeV level the net resonant attenuation in nitrogenous explosives is about 2% per centimeter of explosive.

It has further been found in accordance with the present invention that the net resonant attenuation is readily detectable by a conventional $\gamma$-ray detector provided the detection medium therein contains nitrogen. Such a detector, which may be described as a resonant detector, selects the relevant energy portion of the transmitted flux spectrum which contains the resonant absorption information.

Based on all this, the present invention provides a method for the detection of a nitrogenous explosive material in an object, comprising:

(i) placing on one side of the object a source for 9.17 MeV $\gamma$-rays adapted to produce the desired photon flux (emitted flux);

(ii) placing on the opposite side of the object a $\gamma$-ray detector or array of detectors with a nitrogen rich detection medium;

(iii) scanning the object with a $\gamma$-ray beam from said source;

(iv) reading from said $\gamma$-ray detector or array of detectors the total and the non-resonant attenuations of the incident photon flux; and (v) deriving from said attenuations the net resonant attenuation and the spatial distribution thereof.

The spatial distribution data ma be processed and interpreted in terms of the presence of absence of explosives and/or benign nitrogen-containing materials within the inspected object.

The net resonant component of attenuation is directly proportional to the amount of nitrogenous explosive present in the inspected object. Preferably the attenuation is computed automatically by a suitable comparator device of known design and the output of such a device may be so calibrated as to give directly quantitative indications of the amount of explosives in the object.

The invention further provides a system for the detection of a nitrogenous explosive material in an inspected object by the above method, comprising:

(i) a radiation source for 9.17 MeV γ-rays;

(ii) a γ-radiation detector with a nitrogen-rich detection medium and adapted to show modulations of the detected photon flux;

(iii) holder means for holding the inspected object so as to intercept the gamma radiation from said γ-radiation source; and (iv) means for scanning the inspected object with the said 9.17 MeV γ-rays.

For scanning the inspected object the said holder means may be movable whereby the inspected object is gradually shifted through the γ-ray beam in such a way that the entire cross-section thereof is successively exposed. This may be accomplished by associating the above system with mechanical means such as a conveyor belt for continuously or intermittently feeding and removing objects to be inspected.

Alternatively the emitter and detector may be moved synchronically so that the beam suitably scans the object.

In accordance with one embodiment the above system comprises processor means for continuously comparing the detected photon flux with the emitted photon flux. If desired, such processor means may be adapted to interpret any flux modulations obtained by scanning an object.

DESCRIPTION OP THE DRAWINGS

In the following some specific embodiments of the invention will be described with reference to the annexed drawings in which:

FIGS. 2a–2d are graphical representations in which the cross-section for absorption, incident flux, transmitted flux and detection efficiency are plotted against energy;

DESCRIPTION OF SPECIFIC EMBODIMENTS

Figure 1:
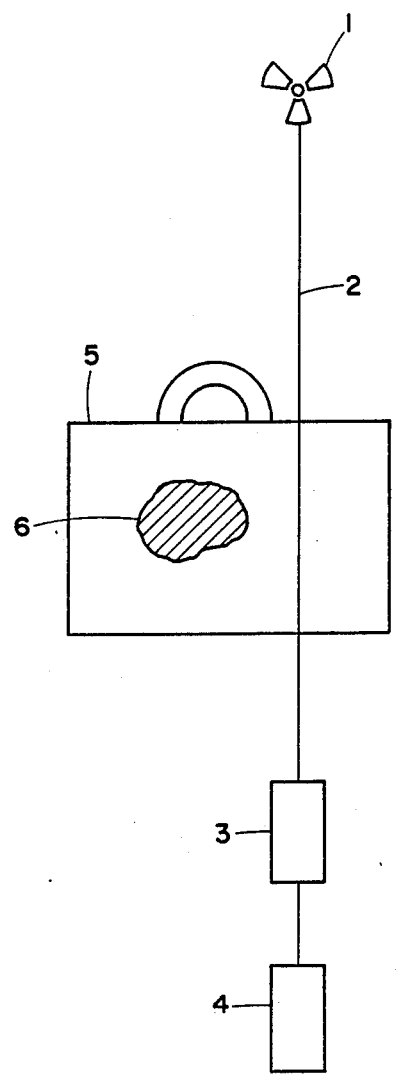
FIG. 1 is a diagramatic illustration of a system according to the invention.

The method according to the invention is best explained with reference to FIG. 1. As shown, a γ-ray source 1 emits γ-rays of a desired and monitored flux, symbolized by line 2, so as to impinge on a γ-ray detector 3 electrically linked to a recorder 4. Detector 3 is designed to produce electric signals in response to incident γ-rays and any current modulations are recorded and displayed by recorder 4.

An object 5 held by means of suitable holder means (not shown) is successively moved across beam 2. The object 5 is shown to contain a body of a nitrogenous explosive 6. As long as body 6 does not intersect beam 2 the gamma rays pass across the object without any resonant attenuation. Once however, body 6 crosses beam 2 the resonant flux detected by detector 3 is attenuated and the information is transmitted to recorder 4.

In the performance of the method according to the invention the object 5 is gradually passed across beam 2 so as to be scanned thereby. This may be achieved either by moving the object itself or else by synchronically moving emitter 1 and detector 3.

An ideal γ-ray source for the purpose of the present invention would be a source which emits photons that are all concentrated in a 200 electron volt energy interval around the peak of 9.17 MeV so that all of them undergo resonant attenuation in case the inspected object contains a nitrogenous explosive. However such sources are not available and in order to count only resonant photons of 9.17 MeV out of the transmitted fraction of the radiation, one has to use a resonant detector which is sensitive only to photons in the 9.17 MeV ± 100 eV interval.

Source 1 may for example be a device which emits photons upon capture of 1.75 MeV protons in $^{13}C$. This source of 9.17 MeV photons is the closest to the ideal γ-source since the γ-rays emitted at a given angle upon the capture of the protons are monochromatic (doppler shifted but not broadened). In order to construct such a source for an operational facility one needs a proton accelerator capable of delivering a proton current of about 1 mA.

An alternative device that ma be used is the so-called high energy bremsstrahlung source which is commercially available. This radiation source is an electron accelerator capable of producing a broad spectrum of energetic photons. The fraction of resonant photons which can be obtained with such a source is very small (about 5 orders of magnitude smaller than with the previously described source) but accelerators with adequate intensity are readily available.

In detector 3 which, as mentioned above, should hold a nitrogen-rich detection medium, the incident photons react resonantly with the nitrogen medium via the (γ,p) reaction. The resulting 1.5 MeV protons have then to be counted with high discrimination against the numerous compton electrons produced in the detector by photons of all energies.

Two types of detectors may be mentioned. The first are gas detectors (proportional counters or gas scintillators) filled with nitrogen gas. In these detectors the discrimination between the protons and electrons is made by the amount of energy left by the particles in the detector. By limiting the dimensions of the chamber to the range of the 1.5 MeV protons one can ensure that electrons deposit in the counter no more than 50 keV.

The second kind of detectors are scintillators with a liquid detection medium. An adequate resonant liquid scintillator may be made by adding nitrogen-containing compounds to existing liquid scintillators or by using exclusively a scintillating material which contains nitrogen as a constituent of its molecule. Since in these detectors the resonant scintillating medium is denser than in the gas detectors, they are more efficient for detecting γ-rays. Upon interaction with radiation they emit light. The discrimination between protons and electrons is possible on the basis of the difference in the decay time of the produced light, the light produced by protons having a larger decay constant. The commercially available liquid scintillators have organic solvents such as xylene or toluene as scintillation medium. No scintillators with a nitrogenous medium are commercially available, but have been produced in our laboratory.

The cross-section for absorption of a photon by a nitrogenous absorber such as a nitrogenous explosive has a resonance shape at 9.17 MeV as shown in FIG. 2a which plots the cross-section for absorption against energy. In FIG. 2b the incident flux is plotted against energy and in FIG. 2c the transmitted flux is plotted against energy. From these two figures it is readily seen that the portion of incident photon flux in the specific energy interval corresponding to the 9.17 MeV excited state will undergo nuclear resonant absorption whenever the beam encounters a region of high nitrogen concentration in the inspected object. This effect can be quantitatively measured by means of an appropriate detector with a resonant response as specified above and as shown in FIG. 2d which plots the detection efficiency against energy. The detection efficiency which is at its peak in the 9.17 MeV range, drops rapidly to zero on both sides.

As explained above, NRA requires resonant detectors to select the relevant energy portion of the transmitter flux spectrum which contains the resonant absorption information. In accordance with the invention $\gamma$-ray detectors with nitrogen rich detection medium fulfil that function. Since, however, in addition to the resonant attenuation there also occurs a conventional non-resonant attenuation, non-resonant detectors, e.g. NaI or Bismuth Germanate detectors, are required in order to factor-out this component in the spectrum which is then used for normalization purposes.

Figure 3:
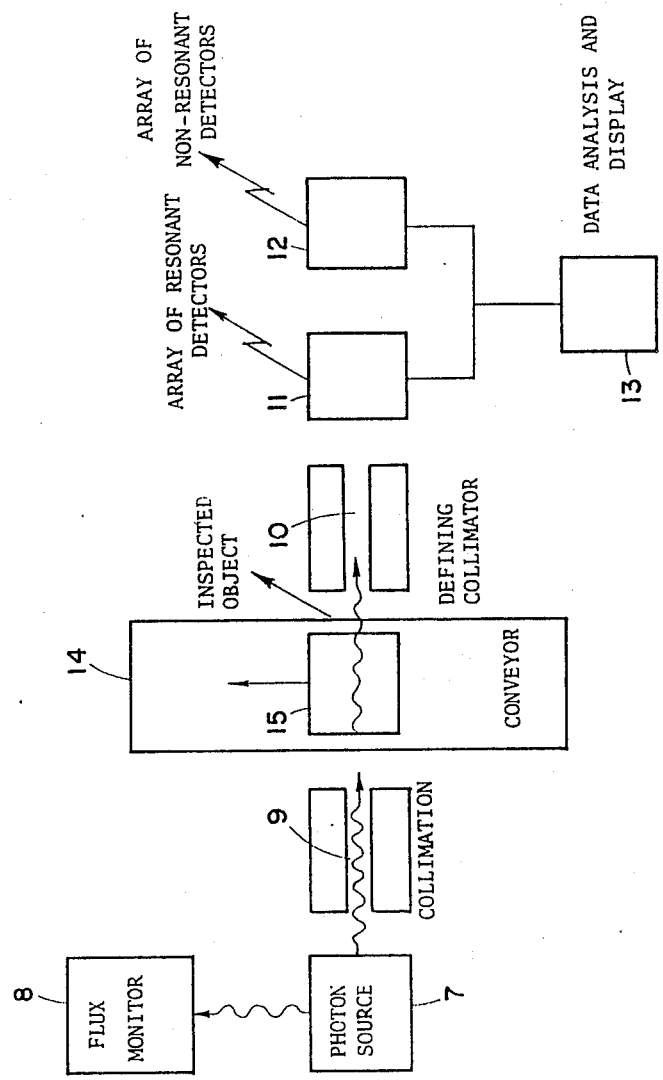
FIG. 3 is a block diagram of a system according to the invention.

FIG. 3 shows a block diagram of an installation according to the invention with resonant and non-resonant detectors. As shown, the system comprises a $\gamma$-ray emitter 7 serving as photon source and linked to a flux monitor 8. There are further provided collimator blocks 9 and 10 for the collimation of the $\gamma$-radiation emitted from source 7 in front of and behind the inspected object. The system further comprises an array 11 of resonant detectors and an array 12 of non-resonant detectors, both linked to a data analysis and display device 13 which is also linked to the flux monitor in a manner not shown.

The system is associated with a conveyor 14 adapted to move successively a plurality of objects such as object 15 across the beam emitted by photon source 7. After its encounter with an object 15 the passing radiation is once more collimated by collimator lens 10 and is thereupon analysed by the assembly of resonant detectors 11, non-resonant detectors 12 and data analysis devices 13.

Instead of non-resonant detectors, it is also possible in accordance with the invention to make use of Compton electrons produced in the resonant detector by photons of all energies for factoring out the non-resonant attenuation component.

The feasibility of the NRA method according to the invention was demonstrated in the laboratory using thin melamine absorbers (67% nitrogen). The resonant detector was laboratorymade and consisted of a commercially available liquid scintillator (NE-213), mixed with acetonitrile (34% nitrogen). The nitrogen content of the mixture was 10% wt/wt.

Figure 4:
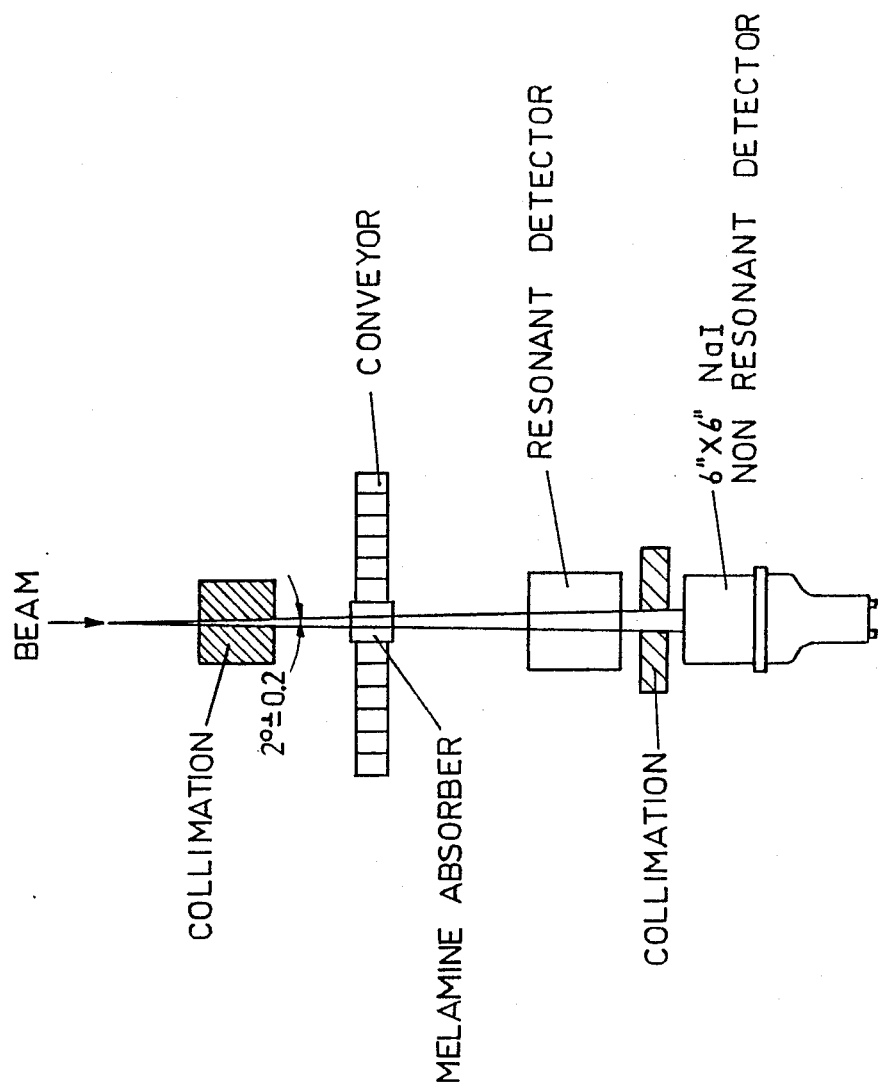
FIG. 4 is a diagrammatic illustration of an experimental model arrangement for showing the feasibility of the NRA method according to the invention.

The experimental arrangement is shown in FIG. 4. The melamine absorber was mounted on a conveyor and was inserted in and out of a 9.17 MeV $\gamma$-ray beam. The non-resonant attenuation was measured by a 6"×6"NaI detector positioned behind the resonant detector. The following Table summarizes the results obtained in the experiment.

| Melamine thickness (cm) | Net resonant attenuation (%) |
| --- | --- |
| 0 | 0.6 + 1.3 |
| 1.2 | 3.2 + 1.2 |
| 2.4 | 7.6 + 1.5 |

This demonstration shows that given sufficient statistical precision, it is possible to detect thin absorbers significantly and quantitatively. However, for higher sensitivity scintillators with solvents of higher nitrogenous content should be used.

What is claimed is:

1. A method for the detection of a nitrogenous explosive material in an object, comprising:
   (i) placing on one side of the object a source for 9.17 MeV $\gamma$-rays adapted to produce a desired photon flux (emitted photon flux);
   (ii) placing on the opposite side of the object a $\gamma$-ray detector or array of detectors with a nitrogen rich detection medium;
   (iii) scanning the object with a $\gamma$-ray beam from said source;
   (iv) reading from said $\gamma$-ray detector or array of detectors the total and the non-resonant attenuations of the incident photon flux; and
   (v) deriving from said attenuations the net resonant attenuation and the spatial distribution thereof.

2. A method according to claim 1 comprising interpreting the said net resonant attenuation to derive a quantitative reading of any detected nitrogen.

3. A system for the detection of a nitrogenous explosive material in an object, comprising:
   (i) a source for 9.17 MeV $\gamma$-rays;
   (ii) a $\gamma$-ray detector with a nitrogen-rich detection medium and adapted to show modulations of the detected photon flux;
   (iii) holder means for holding an inspected object so as to intersect the $\gamma$-rays from said source for 9.17 MeV $\gamma$-rays; and
   (iv) means for scanning the inspected object with the $\gamma$-rays emitted by said source for 9.17 MeV $\gamma$-rays.

4. A system according to claim 3 in which said holder means are movable whereby an inspected object is scanned by the $\gamma$-rays.

5. A system according to claim 4, wherein said holder means is a conveyor belt adapted to move a succession of objects for inspection across the $\gamma$-rays.

6. A system according to claim 3 in which the $\gamma$-ray source and detector are movable synchronically whereby an inspected object is scanned by the $\gamma$-rays.

7. A system according to claim 3, comprising processor means for continuously comparing the detected photon flux with the emitted photon flux.

8. A system according to claim 7, wherein said processor means are adapted to interpret any flux modulations obtained by scanning an object.

* * * * *